(12) United States Patent
McSwiney et al.

(10) Patent No.: US 7,470,450 B2
(45) Date of Patent: Dec. 30, 2008

(54) FORMING A SILICON NITRIDE FILM

(75) Inventors: Michael L. McSwiney, Hillsboro, OR (US); Mansour Moinpour, San Jose, CA (US); Michael D. Goodner, Hillsboro, OR (US)

(73) Assignee: Intel Corporation, Santa Clara, CA (US)

( * ) Notice: Subject to any disclaimer, the term of this patent is extended or adjusted under 35 U.S.C. 154(b) by 831 days.

(21) Appl. No.: 10/764,193

(22) Filed: Jan. 23, 2004

(65) Prior Publication Data

US 2005/0163927 A1 Jul. 28, 2005

(51) Int. Cl.
*C23C 16/00* (2006.01)
(52) U.S. Cl. .................. 427/255.394; 427/255.18; 427/255.28; 427/248.1; 427/255.23
(58) Field of Classification Search .......... 427/248.1, 427/532, 255.393, 255.394, 255.395, 226, 427/255.27, 255.39; 438/780, 781, 783, 438/623
See application file for complete search history.

(56) References Cited

U.S. PATENT DOCUMENTS

| | | | | |
|---|---|---|---|---|
| 4,720,532 A | * | 1/1988 | Seyferth et al. ............... | 528/28 |
| 5,041,303 A | * | 8/1991 | Wertheimer et al. ......... | 427/575 |
| 2002/0016084 A1 | * | 2/2002 | Todd ........................... | 438/791 |
| 2006/0228903 A1 | * | 10/2006 | McSwiney et al. .......... | 438/778 |

OTHER PUBLICATIONS

Bao et al. "Polycyclodisilazane: a new polymeric precursor for silicon nitride-based ceramics" Journal of Materials Chemistry, 2000, 10, 395-401.*
Scarlete et al. "Poly(methylsilane) and Poly(Hydrazinomethylsilane) as precursors for silicon containing ceramics", NATO ASI Series, Series E: Applied Science (1995) 125-140.*
Inventors: Michael L. McSwiney and Michael D. Goodner, Patent Application entitled: *Low-Temperature Silicon Nitride Deposition*, filed Jul. 30, 2003, U.S. Appl. No. 10/631,627, Patent Application has 15 pages and 4 pages of drawings.
Author: Schumacher, A Unit of Air Products and Chemicals, Inc.; entitled: *BTBAS Silicon Nitride*; 1 page; www.schumacher.com/btbas, date unknown.

* cited by examiner

*Primary Examiner*—Timothy H Meeks
*Assistant Examiner*—David Turocy
(74) *Attorney, Agent, or Firm*—Trop, Pruner & Hu, P.C.

(57) ABSTRACT

A silicon nitride film may be deposited on a work piece using conventional deposition techniques and a selected source for use as a silicon precursor. A nitrogen precursor may also be selected for film deposition. Using the selected precursor(s), the temperature for deposition may be 500° C., or less.

3 Claims, 7 Drawing Sheets

FORMING A SILICON NITRIDE FILM

BACKGROUND

The present invention relates to forming films during semiconductor device/integrated circuit fabrication and more particularly to depositing silicon nitride films during fabrication.

Semiconductor devices may include several layers deposited or grown on a semiconductor substrate. For example, dielectric layers may be formed to separate metal layers. Two dielectrics widely used in semiconductor device and integrated circuit design include silicon dioxide and silicon nitride.

Silicon nitride may be preferred to silicon dioxide in certain applications. For example, a silicon nitride film may be preferred as a final passivation layer to protect against device contamination. Further, silicon nitride may be preferred material for barrier layers and etch stops.

To create local areas of oxidation on silicon for isolation purposes, a silicon nitride layer may be deposited on a silicon substrate. The silicon nitride layer may be patterned to create islands of silicon nitride separated by silicon. Thereafter, exposed silicon is oxidized. In contrast, silicon beneath the silicon nitride is not oxidized. After patterned oxidation, the remaining silicon nitride may be removed. As such, regions of the substrate surface are separated by isolating regions of oxide. In sum, silicon nitride films may be used in a variety of applications including front and back end processing.

Historically, the use of silicon nitride films was limited due to the high temperatures needed for deposition using conventional techniques and deposition precursors. In fact, deposition of silicon nitride at temperatures above 660° C. may cause damage to devices or components including alloying of aluminum.

Thus, there continues to be a need to improve silicon nitride deposition techniques especially silicon nitride deposition at low temperatures.

DETAILED DESCRIPTION

In accordance with one embodiment of the present invention, a layer such as a silicon nitride layer may be formed at a relatively low temperature using a selected silicon precursor. Examples of selected silicon precursors include cyclodisilazane and sources containing hydrazine moieties such as 1,2, 4,5-tetraaza-3,6-disilacyclohexane and linear hydrazines including two or more silyl substitutions.

Derivatives of each of the aforementioned silicon precursors may also be selected as silicon precursors for silicon nitride deposition. For example, cyclodisilazane may be substituted with a combination of one or more of halogens, amines, silyls, alkyls, aryls or other organic groups having one to about 20 carbon atoms. Further, 1,2,4,5-tetraaza-3,6-disilacyclohexane may also be substituted with a combination of one or more halogens, amines, silyls, alkyls, aryls or other organic groups having one to about 20 carbon atoms. Selected silicon precursors may also include substituted disilyl hydrazines. For example, disilyl hydrazines may be substituted with a combination of one or more of halogens, amines, silyls, alkyls, aryls or other organic groups having one to about 20 carbon atoms.

Figure 1:
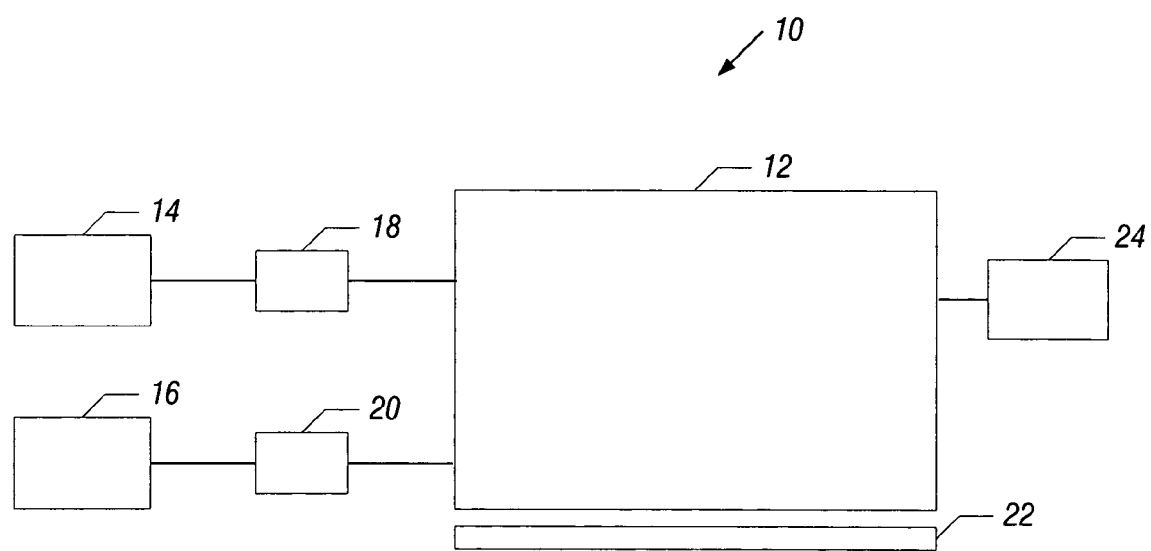
FIG. 1 is a simplified schematic of a deposition chamber according to some embodiments of the present invention.

According to embodiments of the present invention, the silicon nitride film may be deposited using a conventional deposition technique such as chemical vapor deposition (CVD), plasma enhanced chemical vapor deposition (PECVD), atomic layer deposition (ALD) or by vertical diffusion furnace (VDF). Referring to FIG. 1, a system 10, which is shown in a simplified schematic form, may be used to form a silicon nitride film. The system 10 may include a chamber 12 where formation of a silicon nitride film takes place. For example, one or more work pieces (not shown) may be loaded in the chamber 12 for deposition thereon. A selected silicon precursor may be introduced into the chamber 12 from a silicon source 14. Further, a nitrogen precursor may be introduced into chamber 12 via a nitrogen source 16. Additional reactants or aids may be introduced into the chamber 12 as needed via a separate source (not shown).

Meters 18 and 20 may control the entry of the silicon precursor and the nitrogen precursor into the chamber 12 respectively. Alternately or additionally, precursor entry may be controlled by one or more valves (not shown).

A heat source 22 may heat work pieces and/or the chamber 12. Examples of heat sources include radio frequency (RF) induction, furnace, radiant heat source or hot plate, although embodiments are not limited in this respect. Preferably, the temperature should not exceed 500° C., although embodiments are not so limited. In this way, damage to heat sensitive structures or components may be reduced or eliminated. Temperature and pressure sensors (not shown) may monitor temperature and pressure respectively. Further, in certain embodiments, a pump 24, such as a vacuum pump may be connected to the chamber 12. In some embodiments the pump 24 may be an exhaust pump. After the silicon nitride film is deposited, the work piece(s) may be further processed as is known in the art.

As shown in FIG. 1, in some embodiments of the present invention, the selected silicon precursor and the nitrogen precursor may be separately introduced into the deposition chamber 12. Alternately, the selected silicon precursor and the nitrogen precursor may be introduced into the reaction chamber 12 as pre-mixed cocktail. In embodiments where the nitrogen precursor and silicon precursor are introduced into the chamber 12 as a premixed cocktail, the cocktail may also include an optional solvent. The solvent may be an organic solvent such as a hexane, octane or nonane, although embodiments are not limited in this respect.

Typically, nitrogen and silicon are not introduced into the chamber 12 in proportionate amounts. That is, silicon nitride has a ratio of 4 nitrogen to 3 silicon ($Si_3N_4$). Thus, in certain cases, the proportion of nitrogen precursor to silicon precursors is adjusted to yield a film with the same or similar ratio. However, it is not necessary to have a disproportionate amount of precursors. Further, in some embodiments the highly reactive silicon precursor may also be the source of nitrogen. For example, 1,2,4,5-tetraaza-3,6-disilacyclohexane and derivatives thereof, have a nitrogen to silicon ratio that is at least 2:1. This ratio is greater than the stoichiometry of the final silicon nitride film. Thus, in some embodiments, the silicon source and the nitrogen source are one in the same.

Nitrogen sources used as precursors may include hydrazine or a substituted hydrazine(dimethyl hydrazine and t-butyl hydrazine as two examples), although embodiments are not so limited. Further, ammonia may be introduced into the chamber 12 as a nitrogen precursor and/or a catalyst.

Precursor choice, pressures, temperature and gas flow rates may all be adjusted to obtain a desired silicon film. That is, deposition parameters may be adjusted to produce a silicon nitride film having properties that are desired in a particular application. For example, the degree of stress in the silicon nitride film may be tuned over a wide range. One factor that may influence the stress characteristics of the film is the presence of impurities. The type and degree of impurity in a silicon nitride film may be influenced by the choice of highly reactive silicon precursor. For example, in certain embodiments carbon may be a desirable impurity. Thus, a highly reactive silicon precursor containing carbon, such as one including one or more alkyl groups, may be the precursor of choice for that application.

Figure 2A:
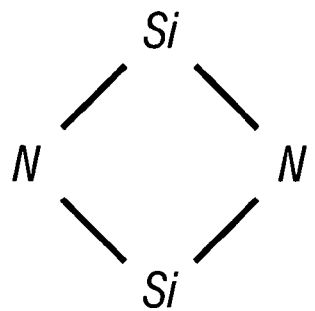
FIGS. 2A-2C are the chemical structures for certain silicon precursors in accordance with some embodiments of the present invention.
Figure 2B:
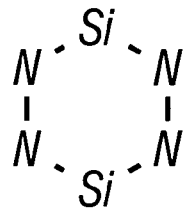
Figure 2C:
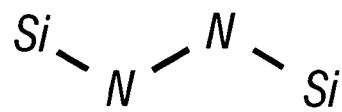

Generally, suitable silicon sources for use as silicon precursors permit silicon nitride deposition at temperatures at or below 500° C. For example, as shown in FIG. 2A, in some embodiments, cyclodisilazane may serve as a source for use as a silicon precursor in some embodiments. Cyclodisilazane includes alternating nitrogen and silicon atoms in a strained four-membered ring. The strain in the four-membered ring makes cyclodisilazane a very reactive silicon source precursor. In other embodiments, the silicon source for use as selected silicon precursor may include a hydrazine ($N_2H_4$) moiety as shown in FIGS. 2B and 2C. In certain embodiments, hydrazine may be found in a strained ring system such as in 1,2,4,5-tetraaza-3,6-disilacyclohexane, as shown in FIG. 2B. Alternately, in other embodiments the selected silicon precursor may be a linear hydrazine in the form of a disilyl substituted hydrazine (1,2-disilylhydrazine), as shown in FIG. 2C.

Figure 3A:
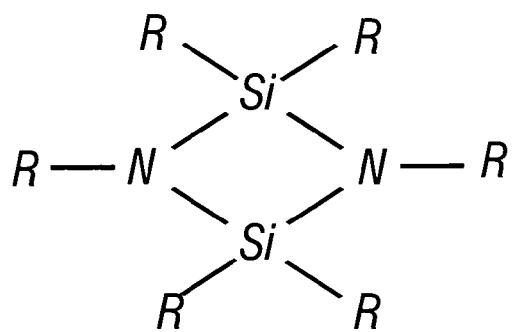
FIG. 3A is a structure which shows where one or more substitutions may occur on the silicon precursor of FIG. 2A to yield derivatives for use as silicon precursors in the formation of silicon nitride films.

Referring to FIGS. 3A-3L, a few examples of cyclodisilazane derivatives that may be suitable sources for use as silicon precursors in some embodiments of the present invention are shown, although embodiments are not so limited. Generally, the family of cyclodisilazane derivatives may have the general formula [$R_2SiNR$]$_2$, which is schematically shown in FIG. 3A, where R may be any one or more of hydrogen, halogens, amines, alkyls, aryls, silyls or other organic groups containing one to about twenty carbon atoms. That is, each R group is independent from the other and may be selected from the aforementioned groups.

Figure 3B:
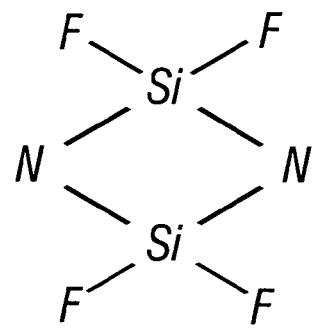
FIGS. 3B-3L show representative substitutions of the silicon precursor of FIG. 2A that may be selected as sources for silicon precursors according to some embodiments of the present invention.
Figure 3C:
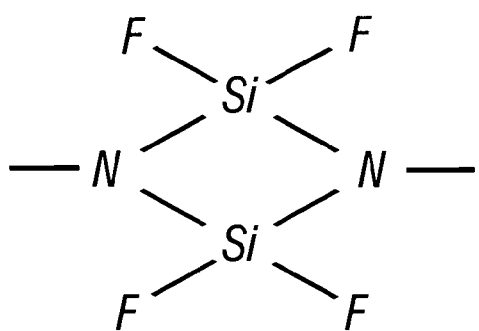
Figure 3D:
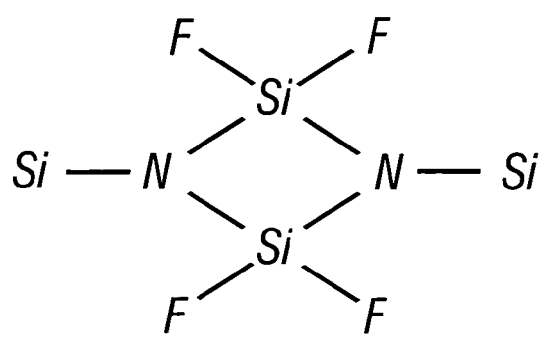

Referring to FIGS. 3B-3D, in certain embodiments, the source for use as a silicon precursor may be a halogenated cyclodisilazane. In the embodiments shown, cyclodisilazane is partially substituted with at least one halogen. The halogenated precursor may include additional substitutions. Specifically, referring to FIGS. 3B-3D, certain selected cyclodisilazane derivatives for use as silicon precursors include at least one fluorine substitution to yield 1,1,3,3 tetraflourocyclodisilazane, 1,1,3,3-tetrafluoro-2,4-dimethylcyclodisilazane and 1,1,3,3-tetrafluoro-2,4-disilylcyclodisilazane respectively.

Figure 3E:
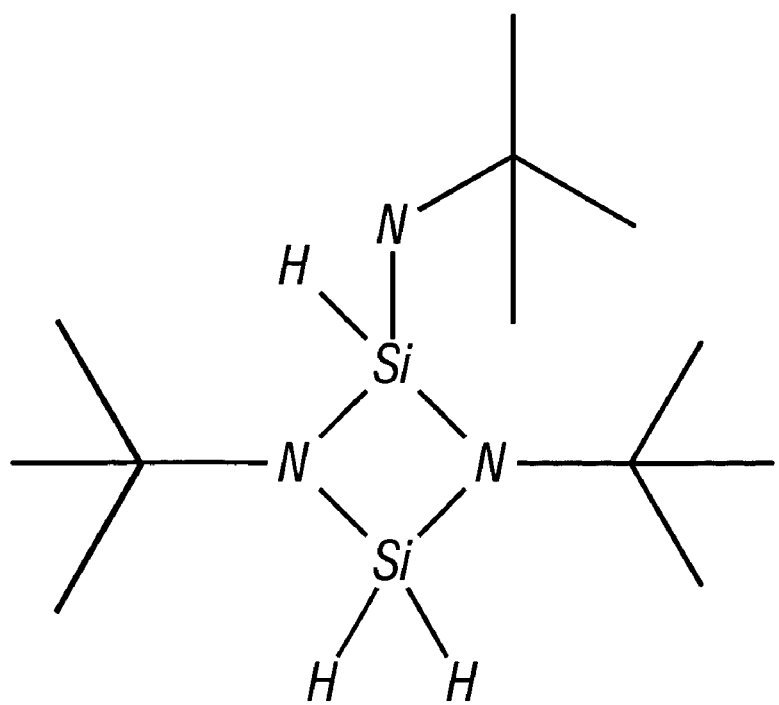
Figure 3F:
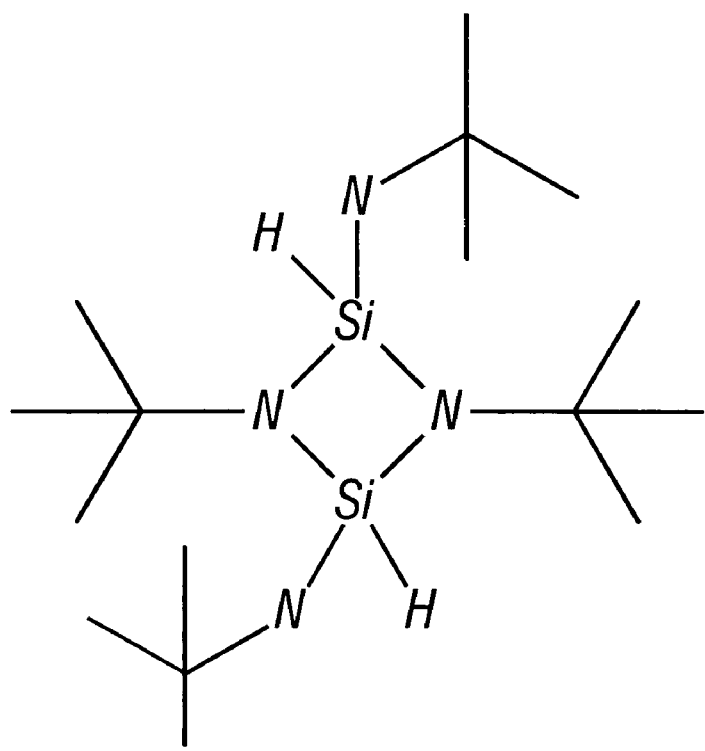
Figure 3G:
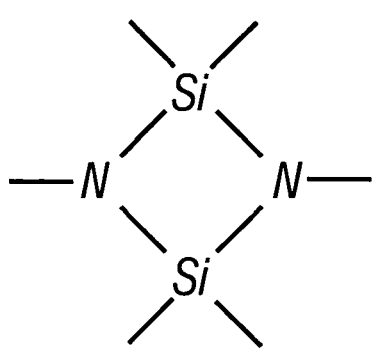
Figure 3H:
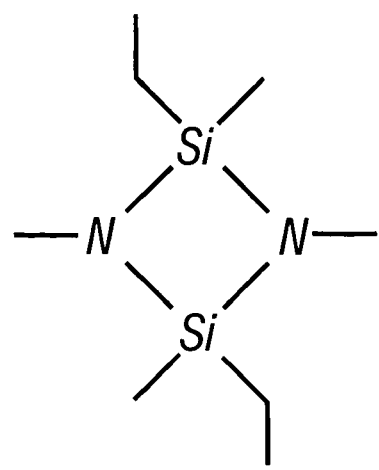
Figure 3I:
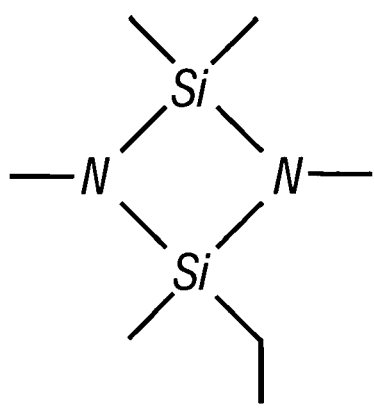
Figure 3J:
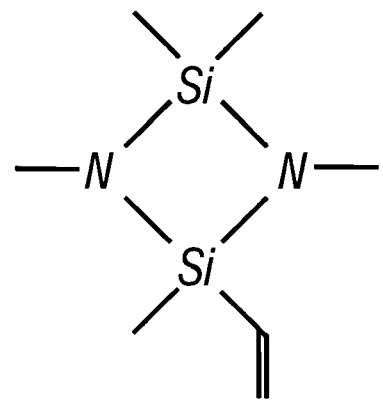
Figure 3K:
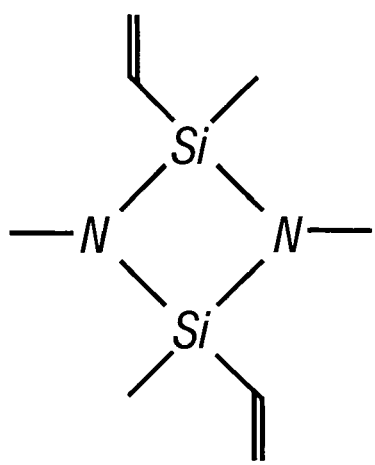

Referring to FIGS. 3E-3F, in some embodiments the selected source for use as a silicon precursor may be an amine substituted cyclodisilazane. Specifically, as shown in FIGS. 3E and 3F respectively 1-tertiarybutylamino-2,4-ditertiarybutylcyclodisilazane and 1,3-ditertiarybutylamino-2,4-ditertiarybutylcyclodisilazane may be suitable silicon precursors, although embodiments are not so limited.

Figure 3L:
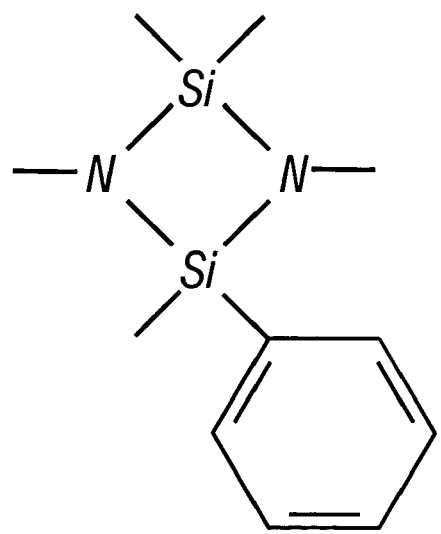

Referring to FIGS. 3G-3L, in some embodiments cyclodisilazane may be partially or fully substituted with one or more organic groups to give rise to suitable silicon sources for use as silicon precursors in silicon nitride deposition. For example, as shown in FIGS. 3G-3K cyclodisilazane may include one or more alkyl substitutions. In certain embodiments, 1,1,2,3,3,4-hexamethylcyclodisilazane, 1,3-diethyl-1,2,3,4-tetramethylcyclodisilazane, 1-ethyl-1,2,3,3,4-pentamethylcyclodisilazane, 1-vinyl-1,2,3,3,4-pentamethylcyclodisilazane, 1,3-divinyl-1,2,3,4-tetramethylcyclodisilazane as shown in FIGS. 3G-3K respectively, may be suitable silicon precursors although alkyl substituted cyclodisilazanes are not so limited. Further, as shown in FIG. 3L cyclodisilazane may be substituted with one or more aryl groups. For example, 1-phenyl-1,2,3,3,4-pentamethylcyclodisilazane may be a suitable source for use as a silicon precursor, although embodiments are not limited in this respect.

Figure 4A:
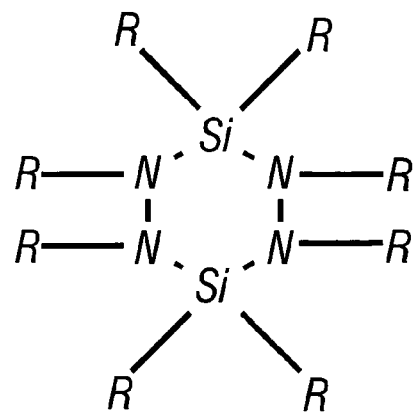
FIG. 4A is a structure that shows where one or more substitutions may occur on the silicon precursor of FIG. 2B to yield derivatives that may serve as silicon sources for silicon nitride formation.
Figure 4B:
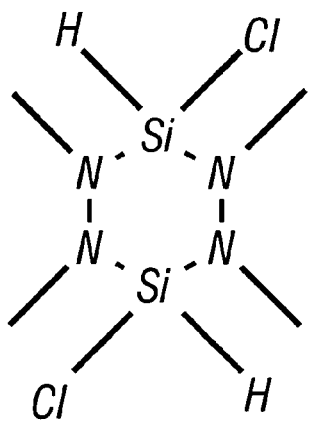
FIGS. 4B-4J show representative substitutions of the silicon precursor of FIG. 2B that may be selected as suitable silicon source precursors in accordance with some embodiments of the present invention.
Figure 4C:
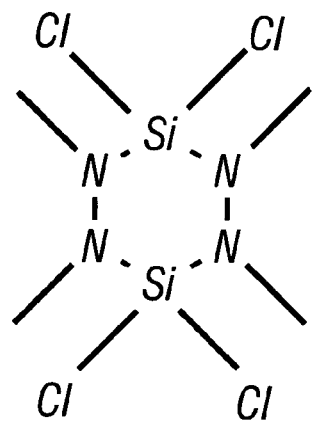

Referring to FIG. 4A, in some embodiments of the present invention, derivatives or variants of normal 1,2,4,5-tetraaza-3,6-disilacyclohexane may be suitable sources for use as silicon precursors to deposit a silicon nitride layer. Suitable derivatives may include substitutions at any one or more positions identified by R where each R may be a hydrogen, a halogen, an amine, a silyl, an alkyl, an aryl or another organic groups having one to about 20 carbon atoms, which is explained below. For example, 1,2,4,5-tetraaza-3,6-disilacyclohexane may be halogenated in certain embodiments. Halogenated derivatives of 1,2,4,5-tetraaza-3,6-disilacyclohexane follow the general formula $Si_2N_4R_{8-a}X_a$, where X is used to specifically designate a halogen, R may be one or more of the groups mentioned above such as but not limited to hydrogen, alkyls, aryls, silyls, and amines, and a is an integer from one up to and including eight. Two representative halogenated derivatives that are suitable for use as silicon precursors are shown in FIGS. 4B and 4C, which are 3,6-dichloro-1,2,4,5-tetramethyl-1,2,4,5-tetraaza-3,6-disilacyclohexane and 3,3,6,6-tetrachloro-1,2,4,5-tetramethyl-1,2,4,5-tetraaza-3,6-disilacyclohexane respectively, although embodiments are not so limited.

Figure 4D:
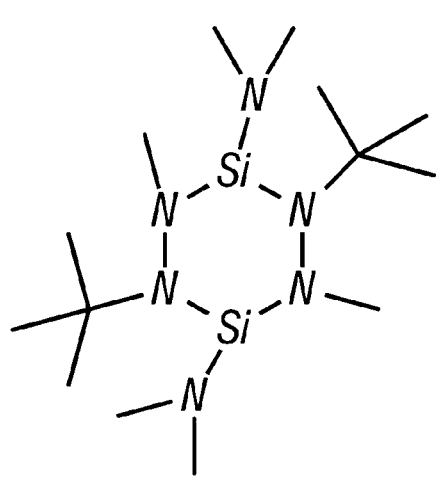
Figure 4E:
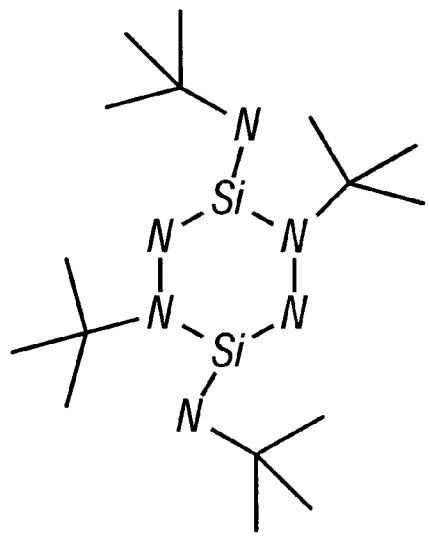

Referring to FIGS. 4D and 4E, variants of 1,2,4,5-tetraaza-3,6-disilacyclohexane having amine functional groups may have the general formula $Si_2N_4R_{8-a}(NR_2)_a$, where a may be 1, 2, 3 or 4 and R may be one or more of the aforementioned R groups including but not limited to hydrogen, halogens, alkyls, aryls, silyls and other organic functional groups. In some embodiments the source for use as the silicon precursor may be 3,6-bis(dimethylamino)-1,4-ditertiarybutyl-2,5-dimethyl-1,2,4,5-tetraaza-3,6-disilacyclohexane or 3,6-bis(tertiarybutylamino)-1,4-ditertiarybutyl-1,2,4,5-tetraaza-3,6-disilacyclohexane, as shown in FIGS. 4D and 4E respectively, although embodiments are not limited thereto.

Figure 4F:
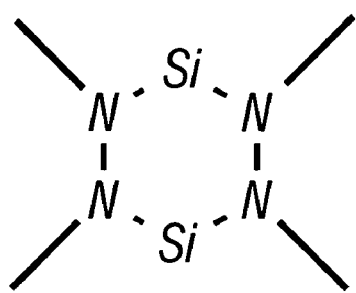
Figure 4G:
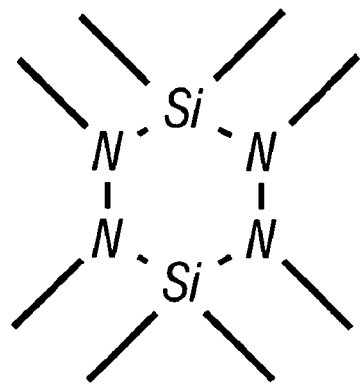
Figure 4H:
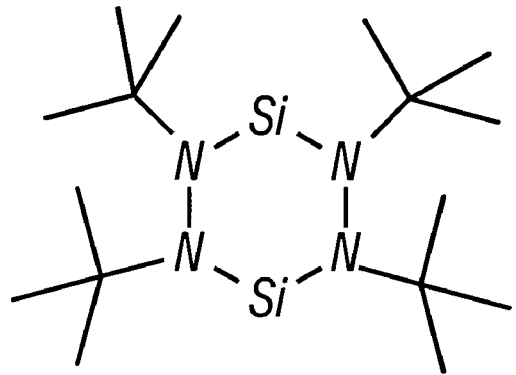
Figure 4I:
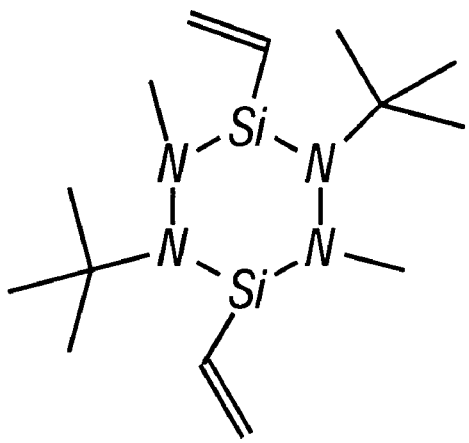
Figure 4J:
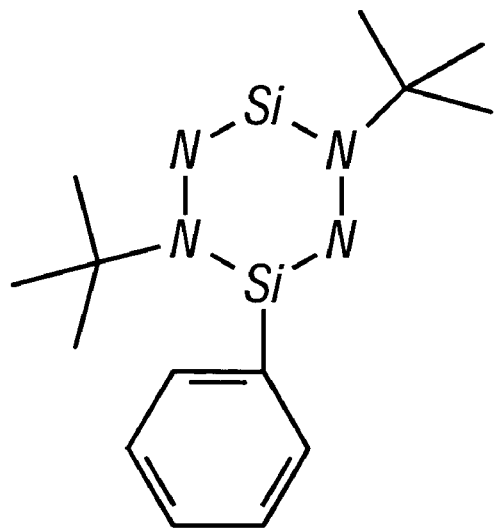

Referring to FIGS. 4F-4J, 1,2,4,5-tetraaza-3,6-disilacyclohexane may be varied by substituting an alkyl and/or aryl group to form a source for use as a suitable silicon precursor. Precursors of this nature have the general formula $Si_2N_4R_8$ where R may be selected from one or more of the aforementioned R groups including hydrogen, halogens, amines, silyls, alkyls, aryls and organic groups having one to about 20 carbon atoms. For example, as shown in FIGS. 4F, 4G and 4H respectively, the normal compound has been substituted with alkyl groups to form 1,2,4,5-tetramethyl-1,2,4,5-tetraaza-3,6-disilacyclohexane, 1,2,3,3,4,5,6,6-octamethyl-1,2,4,5-tetraaza-3,6-disilacyclohexane and 1,2,4,5-tetratertiarybutyl-1,2,4,5-tetraaza-3,6-disilacyclohexane, each of which may be suitable as a source for the silicon precursor in certain embodiments. Further, as shown in FIGS. 4I and 4J, the normal molecule may include vinyl and/or aryl groups to form suitable silicon precursors for silicon nitride deposition. Representative sources for silicon precursors in this group include 3,6-divinyl-1,4-ditertiarybutyl-2,5-dimethyl-1,2,4,5-tetraaza-3,6-disilacyclohexane and 3-phenyl-1,4-ditertiarybutyl-1,2,4,5-tetraaza-3,6-disilacyclohexane as shown in FIGS. 4I and 4J respectively.

Figure 5A:
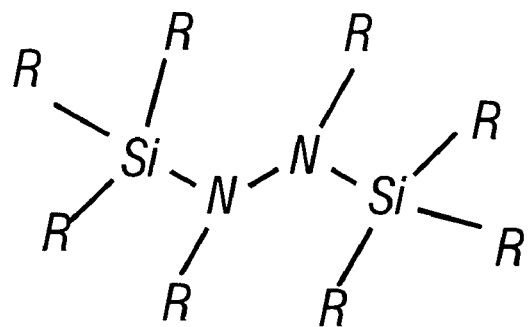
FIG. 5A is a structure that shows where one more substitutions may occur on the silicon precursor of FIG. 2C to yield derivatives that may serve as a silicon source precursor.
Figure 5B:
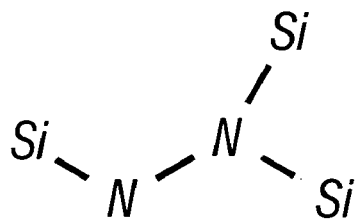
FIGS. 5B-5E show representative substitutions of the silicon precursor of FIG. 2C that may be selected as suitable silicon precursors for formation of silicon nitride films, in accordance with some embodiments of the present invention.
Figure 5C:
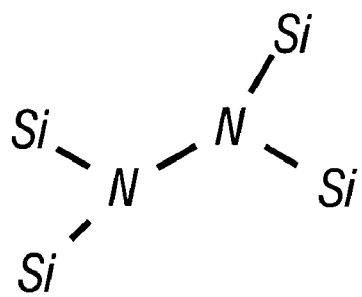
Figure 5D:
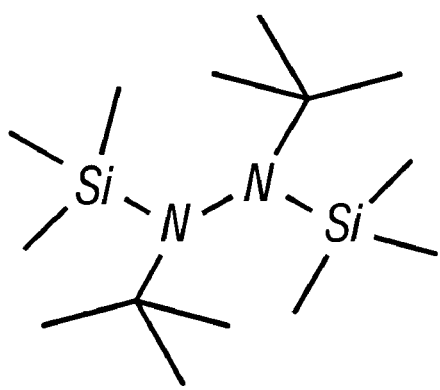
Figure 5E:
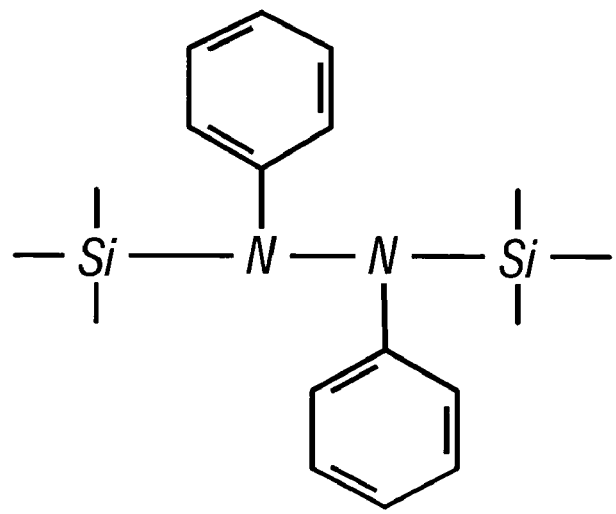

Referring to FIG. 5A, a disilyl substituted hydrazine may serve as the silicon source for silicon precursors for the deposition of a silicon nitride film in some embodiments. Generally, silyl substituted hydrazines have the formula $N_2(SiR_3)_aR_{4-a}$, where a may be 2, 3, or 4 and R may be any group such as hydrogen, halogens, amines, silyls, alkyls, aryls and organic groups having one to about 20 carbon atoms, although embodiments of the invention are not so limited. Representative silyl substituted hydrazines include 1,1,2-trisilylhydrazine, 1,1,2,2-tetrasilylhydrazine, 1,2-bis(trimethylsilyl)-1,2-ditertiarybutylhydrazine and 1,2-bis(trimethylsilyl)-1,2-diphenylhydrazine as shown in FIGS. 5B-5E respectively. Each of the above silyl-substituted hydrazines may serve as a silicon source for use as a silicon precursor to deposit a silicon nitride film, although embodiments are not limited thereto.

While the present invention has been described with respect to a limited number of embodiments, those skilled in the art will appreciate numerous modifications and variations therefrom. It is intended that the appended claims cover all such modifications and variations as fall within the true spirit and scope of this present invention.

What is claimed is:

1. A method comprising:
    using 1,2,4,5-tetraaza-3,6-disilacyolohexane as a silicon precursor to form silicon nitride film at a temperature less than 500° C.

2. The method of claim 1 further including using a nitrogen precursor selected from one of ammonia, a hydrazine or a substituted hydrazine.

3. The method of claim 2 further including combining said silicon precursor and said nitrogen precursor in a premixed cocktail with an optional solvent.

* * * * *

UNITED STATES PATENT AND TRADEMARK OFFICE
CERTIFICATE OF CORRECTION

PATENT NO.       : 7,470,450 B2                                    Page 1 of 1
APPLICATION NO.  : 10/764193
DATED            : December 30, 2008
INVENTOR(S)      : Michael L. McSwiney et al.

It is certified that error appears in the above-identified patent and that said Letters Patent is hereby corrected as shown below:

Col. 6:
Line 19, "1,2,4,5-tetraaza-3,6-disilacyolohexane" should be --1,2,4,5-tetraaza-3,6-disilacyclohexane--.

Signed and Sealed this
Twenty-third Day of October, 2012

David J. Kappos
*Director of the United States Patent and Trademark Office*